(12) United States Patent
Bittner et al.

(10) Patent No.: US 8,596,367 B2
(45) Date of Patent: Dec. 3, 2013

(54) PROCESS FOR PRODUCING MINERAL OIL USING SURFACTANTS BASED ON $C_{16}C_{18}$-CONTAINING ALKYL PROPOXY SURFACTANTS

(75) Inventors: Christian Bittner, Bensheim (DE); Günter Oetter, Frankenthal (DE); Jack Tinsley, Mannheim (DE); Christian Spindler, Ludwigshafen (DE); Gabriela Alvarez-Jürgenson, Mannheim (DE); Sophie Vogel, Mannheim (DE); Veronica Wloka, Mannheim (DE); Marcus Guzmann, Mühlhausen (DE)

(73) Assignee: BASF SE, Ludwigshafen (DE)

( * ) Notice: Subject to any disclaimer, the term of this patent is extended or adjusted under 35 U.S.C. 154(b) by 136 days.

(21) Appl. No.: 13/044,283

(22) Filed: Mar. 9, 2011

(65) Prior Publication Data

US 2011/0220365 A1 Sep. 15, 2011

Related U.S. Application Data

(60) Provisional application No. 61/312,294, filed on Mar. 10, 2010.

(51) Int. Cl.
*E21B 43/00* (2006.01)

(52) U.S. Cl.
USPC ........................................... 166/369

(58) Field of Classification Search
None
See application file for complete search history.

(56) References Cited

U.S. PATENT DOCUMENTS

| | | | |
|---|---|---|---|
| 3,508,612 A | 4/1970 | Reisberg et al. | |
| 3,811,505 A * | 5/1974 | Flournoy et al. | 166/270.1 |
| 3,843,706 A | 10/1974 | Weil et al. | |
| 3,890,239 A | 6/1975 | Dycus et al. | |
| 4,265,264 A | 5/1981 | Sifferman | |
| 4,395,364 A | 7/1983 | Murata et al. | |
| 4,722,396 A | 2/1988 | Balzer | |
| 4,886,120 A | 12/1989 | Shupe | |
| 5,741,947 A | 4/1998 | Wolf et al. | |
| 5,830,831 A * | 11/1998 | Chan et al. | 507/211 |
| 5,849,960 A | 12/1998 | Singleton et al. | |
| 7,462,580 B2 * | 12/2008 | Kirsner et al. | 507/138 |
| 2008/0194435 A1 | 8/2008 | Huff et al. | |
| 2009/0264598 A1 * | 10/2009 | Bittner et al. | 525/231 |
| 2009/0270281 A1 | 10/2009 | Steinbrenner | |
| 2010/0331510 A1 | 12/2010 | Reichenbach-Klinke | |

FOREIGN PATENT DOCUMENTS

| | | |
|---|---|---|
| DE | 4325237 A1 | 2/1995 |
| DE | 10243361 A1 | 4/2004 |
| EP | 003183 A1 | 7/1979 |
| EP | 0207312 A2 | 1/1987 |
| GB | 2054635 A | 2/1981 |
| GB | 2169894 A | 7/1986 |
| WO | WO-2006/131541 A1 | 12/2006 |

OTHER PUBLICATIONS

Gilje, Eiumnd, Branched Ether Surfactant and Their Use in an Enhanced Oil Recovery Process, Oct. 17, 1991, World Intelectual Property Organization, WO 91/15290.*
U.S. Appl. No. 12/903,441, filed Oct. 13, 2010, Bittner et al.
U.S. Appl. No. 12/903,654, filed Oct. 13, 2010, Bittner et al.
U.S. Appl. No. 12/903,762, filed Oct. 13, 2010, Bittner et al.
U.S. Appl. No. 12/950,646, filed Nov. 19, 2010, Steiner et al.
U.S. Appl. No. 13/044,345, filed Mar. 9, 2011, Bittner et al.
U.S. Appl. No. 13/043,210, filed Mar. 8, 2011, Bittner et al.
U.S. Appl. No. 13/111,298, filed May 19, 2011, Bittner et al.
U.S. Appl. No. 13/085,248, filed Mar. 9, 2011.
U.S. Appl. No. 13/091,677, filed Apr. 21, 2011, Bittner et al.
U.S. Appl. No. 13/093,356, filed Apr. 25, 2011, Bittner et al.
U.S. Appl. No. 61/312,294.
U.S. Appl. No. 61/315,051.
U.S. Appl. No. 61/325,051.
U.S. Appl. No. 61/327,118, filed Apr. 23, 2010, Bittner et al.
U.S. Appl. No. 61/327,124.
U.S. Appl. No. 61/394,369.
G. Casiraghi, G. Casnati and M. Cornia, Tetrahedron Letters, No. 9, 679-682 (1973).
M. B. Dinger and M. J. Scott describe in Chem. Commun., 1999, 2525/2526.
M. B. Dinger and M. J. Scott, Inorg. Chem. 2000, 39, 1238-1254.
M. B. Dinger and M. J. Scott , Inorg. Chem. 2001, 40, 1029-1036.
M. B. Dinger and M. J. Scott, Eur J. Org. Chem. 2000, 2467-2478.
K. Matloka, A. Gelis, M. Regalbuto, G. Vandegift and M. J. Scott, Dalton Trans., 2005, 3719-3721.
K. Matloka, A. Gelis, M. Regalbuto, G. Vandegift and M. J. Scott , Separation Science and Technology, 41, 2006, 2129-2146.
M. W. Peters, E. J. Werner and M. J. Scott, Inorg. Chem., 2002, 41, 1701-1716.
R. Mitra, M.W. Peters and M. Scott, Dalton Trans., 2007, 3924-3935.
H. Hoffmann et al., Adv. Colloid Interface Sci. 1982, 17, 275-298.
M. R. Rojas et al., Journal of Colloid and Interface Science 342 (2010) 103-109.
Versteeg et al. Chemosphere 24 (1992) 641-662.
U.S. Appl. No. 12/733,370, Reichenbach-Klinke.
U.S. Appl. No. 61/160,124.
U.S. Appl. No. 61/251,310.
U.S. Appl. No. 61/251,314.

(Continued)

*Primary Examiner* — Angela M DiTrani
*Assistant Examiner* — Silvana Runyan
(74) *Attorney, Agent, or Firm* — Novak Druce Connolly Bove + Quigg LLP

(57) ABSTRACT

A process for mineral oil production by means of Winsor Type III microemulsion flooding and an aqueous surfactant formulation are disclosed. The aqueous surfactant formulation containing at least one ionic surfactant of the general formula $R^1$—O—$(CH_2C(CH_3)HO)_m(CH_2CH_2O)_n$—$XY^-M^+$ is injected through injection boreholes into a mineral oil deposit, and crude oil is withdrawn from the deposit through production boreholes.

4 Claims, No Drawings

(56) References Cited

OTHER PUBLICATIONS

U.S. Appl. No. 61/251,315.
U.S. Appl. No. 61/260,031.
U.S. Appl. No. 61/312,292.
U.S. Appl. No. 61/312,299.
U.S. Appl. No. 61/312,302.
U.S. Appl. No. 13/4269,305, filed Mar. 21, 2012, Bittner et al.
International Search Report for International Application PCT/EP2011/053320, mailing date Jun. 28, 2011.

* cited by examiner

PROCESS FOR PRODUCING MINERAL OIL USING SURFACTANTS BASED ON $C_{16}C_{18}$-CONTAINING ALKYL PROPOXY SURFACTANTS

CROSS-REFERENCE TO RELATED APPLICATIONS

This application claims the benefit of U.S. Provisional Application 61/312,294 filed on Mar. 10, 2010, the contents of which are incorporated herein by reference in its entirety.

FIELD OF THE INVENTION

The invention relates to a process for mineral oil production by means of Winsor type III microemulsion flooding, in which an aqueous surfactant formulation comprising at least one ionic surfactant of the general formula $R^1$—O—$(CH_2C(CH_3)HO)_m(CH_2CH_2O)_n$—$XY^-$ $M^+$ is injected through injection boreholes into a mineral oil deposit, and crude oil is withdrawn from the deposit through production boreholes. The invention further relates to ionic surfactants of the general formula.

BACKGROUND OF THE INVENTION

In natural mineral oil deposits, mineral oil is present in the cavities of porous reservoir rocks which are sealed toward the surface of the earth by impervious top layers. The cavities may be very fine cavities, capillaries, pores or the like. Fine pore necks may, for example, have a diameter of only about 1 µm. As well as mineral oil, including fractions of natural gas, a deposit comprises water with a greater or lesser salt content.

In mineral oil production, a distinction is generally drawn between primary, secondary and tertiary production. In primary production, the mineral oil flows, after commencement of drilling of the deposit, of its own accord through the borehole to the surface owing to the autogenous pressure of the deposit.

After primary production, secondary production is therefore used. In secondary production, in addition to the boreholes which serve for the production of the mineral oil, the so-called production bores, further boreholes are drilled into the mineral oil-bearing formation. Water is injected into the deposit through these so-called injection bores in order to maintain the pressure or to increase it again. As a result of the injection of the water, the mineral oil is forced slowly through the cavities into the formation, proceeding from the injection bore in the direction of the production bore. However, this only works for as long as the cavities are completely filled with oil and the more viscous oil is pushed onward by the water. As soon as the mobile water breaks through cavities, it flows on the path of least resistance from this time, i.e. through the channel formed, and no longer pushes the oil onward.

By means of primary and secondary production, generally only approx. 30 to 35% of the amount of mineral oil present in the deposit can be produced.

It is known that the mineral oil yield can be enhanced further by measures for tertiary oil production. A review of tertiary oil production can be found, for example, in "Journal of Petroleum Science of Engineering 19 (1998)", pages 265 to 280. Tertiary oil production includes, for example, thermal methods in which hot water or steam is injected into the deposit. This lowers the viscosity of the oil. The flow medium used may likewise be gases such as $CO_2$ or nitrogen.

Tertiary mineral oil production also includes methods in which suitable chemicals are used as assistants for oil production. These can be used to influence the situation toward the end of the water flow and as a result also to produce mineral oil hitherto held firmly within the rock formation.

Viscous and capillary forces act on the mineral oil which is trapped in the pores of the deposit rock toward the end of the secondary production, the ratio of these two forces relative to one another being determined by the microscopic oil separation. By means of a dimensionless parameter, the so-called capillary number, the action of these forces is described. It is the ratio of the viscosity forces (velocity x viscosity of the forcing phase) to the capillary forces (interfacial tension between oil and water x wetting of the rock):

$$N_c = \frac{\mu v}{\sigma \cos\theta}.$$

In this formula, µ is the viscosity of the fluid mobilizing mineral oil, v is the Darcy velocity (flow per unit area), σ is the interfacial tension between liquid mobilizing mineral oil and mineral oil, and θ is the contact angle between mineral oil and the rock (C. Melrose, C. F. Brandner, J. Canadian Petr. Techn, 58, Oct.-Dec., 1974). The higher the capillary number, the greater the mobilization of the oil and hence also the degree of oil removal.

It is known that the capillary number toward the end of secondary mineral oil production is in the region of about $10^{-6}$ and that it is necessary to increase the capillary number to about $10^{-3}$ to $10^{-2}$ in order to be able to mobilize additional mineral oil.

For this purpose, it is possible to conduct a particular form of the flooding method—what is known as Winsor type III microemulsion flooding. In Winsor type III microemulsion flooding, the injected surfactants should form a Winsor type III microemulsion with the water phase and oil phase present in the deposit. A Winsor type III microemulsion is not an emulsion with particularly small droplets, but rather a thermodynamically stable, liquid mixture of water, oil and surfactants. The three advantages thereof are that a very low interfacial tension a between mineral oil and aqueous phase is thus achieved, it generally has a very low viscosity and as a result is not trapped in a porous matrix, it forms with even the smallest energy inputs and can remain stable over an infinitely long period (conventional emulsions, in contrast, require high shear forces which predominantly do not occur in the reservoir, and are merely kinetically stabilized).

The Winsor type III microemulsion is in an equilibrium with excess water and excess oil. Under these conditions of microemulsion formation, the surfactants cover the oil-water interface and lower the interfacial tension a more preferably to values of $<10^{-2}$ mN/m (ultra-low interfacial tension). In order to achieve an optimal result, the proportion of the microemulsion in the water-microemulsion-oil system, with a defined amount of surfactant, should by its nature be at a maximum, since this allows lower interfacial tensions to be achieved. In this manner, it is possible to alter the form of the oil droplets (interfacial tension between oil and water is lowered to such a degree that the smallest interface state is no longer favored and the spherical form is no longer preferred), and they can be forced through the capillary openings by the flooding water.

When all oil-water interfaces are covered with surfactant, in the presence of an excess amount of surfactant, the Winsor type III microemulsion forms. It thus constitutes a reservoir for surfactants which cause a very low interfacial tension between oil phase and water phase. By virtue of the Winsor type III microemulsion being of low viscosity, it also migrates through the porous deposit rock in the flooding process (emulsions, in contrast, can become trapped in the porous matrix and block deposits). When the Winsor type III microemulsion meets an oil-water interface as yet uncovered with surfactant, the surfactant from the microemulsion can significantly lower the interfacial tension of this new interface, and lead to mobilization of the oil (for example by deformation of the oil droplets).

The oil droplets can subsequently combine to a continuous oil bank. This has two advantages:

Firstly, as the continuous oil bank advances through new porous rock, the oil droplets present there can coalesce with the bank.

Moreover, the combination of the oil droplets to give an oil bank significantly reduces the oil-water interface and hence surfactant no longer required is released again. Thereafter, the surfactant released, as described above, can mobilize oil droplets remaining in the formation.

Winsor type III microemulsion flooding is consequently an exceptionally efficient process, and requires much less surfactant compared to an emulsion flooding process. In Winsor type III microemulsion flooding, the surfactants are typically optionally injected together with co-solvents and/or basic salts (optionally in the presence of chelating agents). Subsequently, a solution of thickened polymer is injected for mobility control. A further variant is the injection of a mixture of thickening polymer and surfactants, co-solvents and/or basic salts (optionally with chelating agent), and then a solution of thickening polymer for mobility control. These solutions should generally be clear in order to prevent blockages of the reservoir.

The requirements on surfactants for tertiary mineral oil production differ significantly from requirements on surfactants for other applications: suitable surfactants for tertiary oil production should reduce the interfacial tension between water and oil (typically approx. 20 mN/m) to particularly low values of less than $10^{-2}$ mN/m in order to enable sufficient mobilization of the mineral oil. This has to be done at the customary deposit temperatures of approx. 15° C. to 130° C. and in the presence of water of high salt contents, more particularly also in the presence of high proportions of calcium and/or magnesium ions; the surfactants thus also have to be soluble in deposit water with a high salt content.

To fulfill these requirements, there have already been frequent proposals of mixtures of surfactants, especially mixtures of anionic and nonionic surfactants.

U.S. Pat. No. 5,849,960 discloses branched alcohols having 8 to 36 carbon atoms. The degree of branching is at least 0.7 and preferably 1.5 to 2.3, where less than 0.5% quaternary carbon atoms are present, and the branches comprise methyl and ethyl groups. Also described is the further processing of the alcohols to give corresponding surfactants, specifically alkoxylates, sulfates or alkoxy sulfates.

EP 003 183 B1 describes surfactants of the general formula R—O-polypropoxy-poly-ethoxy-X where X is a sulfate, sulfonate, phosphate or carboxylic acid group. R in a preferred embodiment is a branched alkyl radical having 10 to 16 carbon atoms, for example an isotridecyl radical.

The use parameters, for example type, concentration and mixing ratio of the surfactants used with respect to one another, are therefore adjusted by the person skilled in the art according to the conditions existing in a given oil formation (for example temperature and salt content).

As described above, mineral oil production is proportional to the capillary number. The lower the interfacial tension between oil and water, the higher it is. The higher the mean number of carbon atoms in the crude oil, the more difficult it is to achieve low interfacial tension.

BRIEF SUMMARY OF THE INVENTION

Suitable surfactants for low interfacial tensions are those which possess a long alkyl radical. The longer the alkyl radical, the better it is possible to reduce the interfacial tensions. However, the availability of such compounds is very limited and these compounds become increasingly sparingly water-soluble.

It is therefore an object of the invention to provide a particularly efficient and soluble surfactant for use for surfactant flooding or preferably Winsor type III microemulsion flooding, and an improved process for tertiary mineral oil production.

Accordingly, a process is provided for tertiary mineral oil production by means of Winsor type III microemulsion flooding, in which an aqueous surfactant formulation comprising at least one ionic surfactant is injected through at least one injection borehole into a mineral oil deposit for the purpose of lowering the interfacial tension between oil and water to <0.1 mN/m, preferably to <0.05 mN/m, more preferably to <0.01 mN/m, and crude oil is withdrawn from the deposit through at least one production borehole, wherein the surfactant formulation comprises at least one surfactant of the general formula

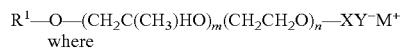

where

R$^1$ is an unbranched, saturated or unsaturated, straight-chain aliphatic hydrocarbon radical having 16 to 18 carbon atoms, n is from 0 to 99, m is from 0 to 99, where the sum of n and m is in the range from 3 to 99, Y$^-$ is selected from the group of sulfate groups, sulfonate groups, carboxylate groups and phosphate groups, X is an alkyl or alkylene group having 0 to 10 carbon atoms, and M$^+$ is a cation.

Additionally provided has been a surfactant mixture for mineral oil production, which comprises at least one ionic surfactant of the general formula defined above.

DETAILED DESCRIPTION OF THE PREFERRED EMBODIMENTS

With regard to the invention, the following should be stated specifically.

In the above-described process according to the invention for mineral oil production by means of Winsor type III microemulsion flooding, an aqueous surfactant formulation comprising at least one surfactant of the general formula is used. It may additionally comprise further surfactants and/or other components.

In the process according to the invention for tertiary mineral oil production by means of Winsor type III microemulsion flooding, the use of the inventive surfactant lowers the interfacial tension between oil and water to values of <0.1 mN/m, preferably to <0.05 mN/m, more preferably to <0.01 mN/m. The interfacial tension between oil and water is thus lowered to values in the range from 0.1 mN/m to 0.0001 mN/m, preferably to values in the range from 0.05 mN/m to 0.0001 mN/m, more preferably to values in the range from 0.01 mN/m to 0.0001 mN/m.

The at least one surfactant can be encompassed by the general formula $R^1$—O—$(CH_2C(CH_3)HO)_m(CH_2CH_2O)_n$—$XY^-M^+$. It is also possible for a plurality of different surfactants of the general formula to be present in the surfactant formulation.

The $R^1$ radical is a straight-chain unbranched aliphatic hydrocarbon radical having 16 to 18 carbon atoms and is preferably saturated.

In the above general formula, n is from 0 to 99, preferably 0 to 19, more preferably 0 to 10.

In the above general formula, m is from 0 to 99, preferably 3 to 20, more preferably 5 to 11.

According to the invention, the sum of n+m is a number in the range from 3 to 99, preferably in the range from 3 to 39, more preferably in the range from 5 to 15.

In a preferred embodiment of the invention, m is greater than n, which means the propylene oxide makes up more than 50% of the overall alkylene oxide (sum of n and m).

In the above-defined general formula n and m are each integers. It is clear to the person skilled in the art in the field of polyalkoxylates that this definition is the definition of a single surfactant. In the case of presence of surfactant formulations which comprise a plurality of surfactants of the general formula, the numbers X and m are each mean values over all molecules of the surfactants, since the alkoxylation of alcohol with ethylene oxide and/or propylene oxide affords a certain distribution of chain lengths. This distribution can be described in a manner known in principle by the polydispersity D. $D=M_w/M_n$ is the quotient of the weight-average molar mass and the number-average molar mass. The polydispersity can be determined by means of the methods known to those skilled in the art, for example by means of gel permeation chromatography.

According to the invention, the ethylene oxide and propylene oxide groups are randomly distributed, alternatingly distributed, or are in the form of two or more blocks in any sequence. More preferably, in the presence of both alkylene oxides in the surfactant the alkylene oxides are >80% arranged in block form, and the propylene oxide block is joined directly to the above-described $R^1$—O.

In the above general formula, X is an alkylene group or alkenylene groups having 0 to 10 and preferably 0 to 3 carbon atoms. In a preferred embodiment of the invention, X is a methylene, ethylene or propylene group.

In the above general formula, Y is a sulfonate, sulfate, carboxylate group or phosphate group. In a preferred embodiment of the invention, r is a sulfate group. The ionic Y group can be attached to the alcohol alkoxylate, for example, by means of sulfation.

In the above formula $M^+$ is a cation, preferably a cation selected from the group of $Na^+$, $K^+$, $Li^+$, $NH_4^+$, $H^+$, $Mg^{2+}$ and $Ca^{2+}$.

The surfactants of the general formula can be prepared in a manner known in principle by alkoxylating corresponding alcohols $R^1$—OH. The performance of alkoxylation is known in principle to those skilled in the art. It is likewise known to those skilled in the art that the molar mass distribution of the alkoxylates can be influenced through the reaction conditions, especially the selection of the catalyst.

The surfactants of the general formula can preferably be prepared by base-catalyzed alkoxylation. The alcohol $R^1$—OH can be admixed in a pressure reactor with alkali metal hydroxides, preferably potassium hydroxide, or with alkali metal alkoxides, for example sodium methoxide. Water still present in the mixture can be drawn off by means of reduced pressure (for example <100 mbar) and/or increasing the temperature (30 to 150° C.). Thereafter, the alcohol is present in the form of the corresponding alkoxide. This is followed by inertization with inert gas (for example nitrogen) and stepwise addition of the alkylene oxide(s) at temperatures of 60 to 180° C. up to a maximum pressure of 10 bar. According to the invention, the propylene oxide is preferably added first, in order to obtain an alkyloxy propylene ether, which is then reacted with the ethylene oxide. At the end of the reaction, the catalyst can be neutralized by adding acid (for example acetic acid or phosphoric acid) and is filtered off if required.

However, the alkoxylation of the alcohols $R^1$—OH can also be undertaken by means of other methods, for example by acid-catalyzed alkoxylation. In addition, it is possible to use, for example double hydroxide clays, as described in DE 432 523 7 A1, or it is possible to use double metal cyanide catalysts (DMC catalysts). Suitable DMC catalysts are disclosed, for example in DE 102 43 361 A1, especially in paragraphs to [0041] and the literature cited therein. For example, it is possible to use catalysts of the Zn—Co type. To perform the reaction, the alcohol $R^1$—OH can be admixed with the catalyst, and the mixture can be dewatered as described above and reacted with the alkylene oxides as described. Typically not more than 1000 ppm of catalyst based on the mixture are used, and the catalyst can remain in the product owing to this small amount. The amount of catalyst may generally be less than 1000 ppm, for example 250 ppm, or less.

The anionic group is finally introduced. This is known in principle to those skilled in the art. In the case of a sulfate group, it is possible, for example, to employ the reaction with sulfuric acid, chlorosulfonic acid or sulfur trioxide in a falling-film reactor with subsequent neutralization. In the case of a sulfonate group it is possible, for example, to employ the reaction with propane sultone and subsequent neutralization, with butane sultone and subsequent neutralization, with vinylsulfonic acid sodium salt, or with 3-chloro-2-hydroxypropanesulfonic acid sodium salt. In the case of a carboxylate group, it is possible, for example, to employ the oxidation of the alcohol with oxygen and subsequent neutralization, or the reaction with chloroacetic acid sodium salt.

Further Surfactants

In addition to the surfactants of the general formula, the formulation may additionally optionally comprise further surfactants. These are, for example, anionic surfactants of the alkylarylsulfonate or olefinsulfonate (alpha-olefinsulfonate or internal olefinsulfonate) type and/or nonionic surfactants of the alkyl ethoxylate or alkyl polyglucoside type. These further surfactants may especially also be oligomeric or polymeric surfactants. It is advantageous to use such polymeric co-surfactants to reduce the amount of surfactants needed to form a microemulsion. Such polymeric co-surfactants are therefore also referred to as "microemulsion boosters". Examples of such polymeric surfactants comprise amphiphilic block copolymers which comprise at least one hydrophilic block and at least one hydrophobic block. Examples comprise polypropylene oxide-polyethylene oxide block copolymers, polyisobutene-polyethylene oxide block copolymers, and comb polymers with polyethylene oxide side chains and a hydrophobic main chain, where the main chain preferably comprises essentially olefins or (meth)acrylates as monomers. The term "polyethylene oxide" here should in each case include polyethylene oxide blocks comprising propylene oxide units as defined above. Further details of such surfactants are disclosed in WO 2006/131541 A1.

Process for Mineral Oil Production

In the process according to the invention for mineral oil production, a suitable aqueous formulation of the surfactants of the general formula is injected through at least one injection borehole into the mineral oil deposit, and crude oil is withdrawn from the deposit through at least one production borehole. The term "crude oil" in this context of course does not mean single-phase oil, but rather the usual crude oil-water emulsions. In general, a deposit is provided with several injection boreholes and with several production boreholes. The main effect of the surfactant lies in the reduction of the interfacial tension between water and oil—desirably to values significantly <0.1 mN/m. After the injection of the surfactant formulation, known as "surfactant flooding", or preferred Winsor type III microemulsion flooding, the pressure can be maintained by injecting water into the formation ("water flooding") or preferably a higher-viscosity aqueous solution of a polymer with strong thickening action ("polymer flooding"). Also known, however, are techniques by which the surfactants are first of all allowed to act on the formation. A further known technique is the injection of a solution of surfactants and thickening polymers, followed by a solution of thickening polymer. The person skilled in the art is aware of details of the industrial performance of "surfactant flooding", "water flooding", and "polymer flooding", and employs an appropriate technique according to the type of deposit.

For the process according to the invention, an aqueous formulation which comprises surfactants of the general formula is used. In addition to water, the formulations may optionally also comprise water-miscible or at least water-dispersible organic substances or other substances. Such additives serve especially to stabilize the surfactant solution during storage or transport to the oil field. The amount of such additional solvents should, however, generally not exceed 50% by weight, preferably 20% by weight. In a particularly advantageous embodiment of the invention, exclusively water is used for formulation. Examples of water-miscible solvents include especially alcohols such as methanol, ethanol and propanol, butanol, sec-butanol, pentanol, butyl ethylene glycol, butyl diethylene glycol or butyl triethylene glycol.

According to the invention, the proportion of the surfactants of the general formula is at least 30% by weight based on the proportion of all surfactants present, i.e. the surfactants of the general formula and optionally present surfactants. The proportion is preferably at least 50% by weight.

The mixture used in accordance with the invention can preferably be used for surfactant flooding of deposits. It is especially suitable for Winsor type III microemulsion flooding (flooding in the Winsor III range or in the range of existence of the bicontinuous microemulsion phase). The technique of Winsor type III microemulsion flooding has already been described in detail at the outset.

In addition to the surfactants, the formulations may also comprise further components, for example $C_4$- to $C_8$ alcohols and/or basic salts (so-called "alkali surfactant flooding"). Such additives can be used, for example, to reduce retention in the formation. The ratio of the alcohols based on the total amount of surfactant used is generally at least 1:1—however, it is also possible to use a significant excess of alcohol. The amount of basic salts may typically range from 0.1% by weight to 5% by weight.

The deposits in which the process is employed generally have a temperature of at least 10° C., for example 10 to 150° C., preferably a temperature of at least 15° C. to 120° C. The total concentration of all surfactants together is 0.05 to 5% by weight, based on the total amount of the aqueous surfactant formulation, preferably 0.1 to 2.5% by weight. The person skilled in the art makes a suitable selection according to the desired properties, especially according to the conditions in the mineral oil formation. It is clear here to the person skilled in the art that the concentration of the surfactants can change after injection into the formation because the formulation can mix with formation water, or surfactants can also be absorbed on solid surfaces of the formation. It is the great advantage of the mixture used in accordance with the invention that the surfactants lead to a particularly good lowering of interfacial tension.

It is of course possible and also advisable first to prepare a concentrate which is only diluted on site to the desired concentration for injection into the formation. In general, the total concentration of the surfactants in such a concentrate is 10 to 45% by weight.

The examples which follow are intended to illustrate the invention in detail:

Part I: Synthesis of the Surfactants Used

General Method 1: Alkoxylation by Means of KOH Catalysis

In a 2 l autoclave, the alcohol to be alkoxylated (1.0 eq) is admixed with an aqueous KOH solution which comprises 50% by weight of KOH. The amount of KOH is 0.2% by weight of the product to be prepared. While stirring, the mixture is dewatered at 100° C. and 20 mbar for 2 h. This is followed by purging three times with $N_2$, establishment of a feed pressure of approx. 1.3 bar of $N_2$ and a temperature increase to 120 to 130° C. The alkylene oxide is metered in such that the temperature remains between 125° C. and 135° C. (in the case of ethylene oxide) or 130 and 140° C. (in the case of propylene oxide). This is followed by stirring at 125 to 135° C. for a further 5 h, purging with $N_2$, cooling to 70° C. and emptying of the reactor. The basic crude product is neutralized with the aid of acetic acid. Alternatively, the neutralization can also be effected with commercial magnesium silicates, which are subsequently filtered off. The light-colored product is characterized with the aid of a $^1$H NMR spectrum in $CDCl_3$, gel permeation chromatography and OH number determination, and the yield is determined.

General Method 2: Sulfation by Means of Chlorosulfonic Acid

In a 1 l round-bottom flask, the alkyl alkoxylate to be sulfated (1.0 eq) is dissolved in 1.5-times the amount of dichloromethane (based on percent by weight) and cooled to 5 to 10° C. Thereafter, chlorosulfonic acid (1.1 eq) is added dropwise such that the temperature does not exceed 10° C. The mixture is allowed to warm up to room temperature and is stirred under an $N_2$ stream at this temperature for 4 h before the above reaction mixture is added dropwise to an aqueous NaOH solution of half the volume at max, 15° C. The amount of NaOH is calculated to give rise to a slight excess based on the chlorosulfonic acid used. The resulting pH is approx. 9 to 10. The dichloromethane is removed at max. 50° C. on a rotary evaporator under gentle vacuum.

The product is characterized by $^1$H NMR and the water content of the solution is determined (approx. 70%).

For the synthesis, the following alcohols were used.

| Alcohol | Description |
|---|---|
| $C_{16}C_{18}$ | Commercially available fatty alcohol mixture consisting of linear $C_{16}H_{33}$—OH and $C_{18}H_{37}$—OH |
| $C_{14}$ | Commercially available linear alcohol $C_{14}H_{29}$—OH |
| $C_{20}$ | Commercially available linear alcohol $C_{20}H_{41}$—OH |

The alcohols were each alkoxylated according to method 1, and the particular degree of alkoxylation is summarized in Tables 1 to 3.

Part II: Performance Tests

The surfactants obtained were used to carry out the following tests in order to assess the suitability thereof for tertiary mineral oil production.

Description of the Test Methods a.) Solubility

An alkyl alkoxy sulfate is dissolved at room temperature in a saline injection water or production water from a deposit (total concentration 500 to 3000 ppm), and NaOH (1000 to 15000 ppm) and optionally a chelating agent, for example EDTA, are added. Optionally, butyl diethylene glycol (BDG) was added. Subsequently, the solution is brought to the deposit temperature. After 24 h, the formulation is assessed visually and used further only in the presence of a clear solution. The injection water of the deposit in question had a salinity of 11250 ppm TDS (total dissolved salt). The deposit temperature was 32° C.

b.) Interfacial Tension

In addition, interfacial tensions were measured directly by the spinning drop method on a dead crude oil (API approx. 14) and the saline original injection water at deposit temperature 32° C. For this purpose, the surfactant solution produced in a) was used. At deposit temperature, an oil droplet was introduced into this clear solution, and the interfacial tension was read off after 2 h.

c.) Determination of SP*

Principle of the Measurement:

The interfacial tension between water and oil was determined in a known manner via the measurement of the solubilization parameter SP*. The determination of the interfacial tension via the determination of the solubilization parameter SP* is a method for approximate determination of the interfacial tension which is accepted in the technical field. The solubilization parameter SP* indicates how many ml of oil are dissolved per ml of surfactant used in a microemulsion (Winsor type III). The interfacial tension a (IFT) can be calculated therefrom via the approximate formula IFT≅0.3/(SP*)$^2$, if equal volumes of water and oil are used. (C. Huh, J. Coll. Interf. Sc., Vol. 71, No. 2 (1979)).

Procedure

To determine the SP*, a 100 ml measuring cylinder with a magnetic stirrer bar is filled with 20 ml of oil and 20 ml of water. To this are added the concentrations of the particular surfactants. Subsequently, the temperature is increased stepwise from 20 to 90° C., and the temperature window in which a microemulsion forms is observed.

The formation of the microemulsion can be assessed visually or else with the aid of conductivity measurements. A triphasic system forms (upper oil phase, middle microemulsion phase, lower water phase). When the upper and lower phase are of equal size and do not change over a period of 12 h, the optimal temperature ($T_{opt}$) of the microemulsion has been found. The volume of the middle phase is determined. The volume of surfactant added is subtracted from this volume. The value obtained is then divided by two. This volume is then divided by the volume of surfactant added. The result is noted as SP*.

The type of oil and water used to determine SP* is determined according to the system to be examined. It is possible either to use mineral oil itself or a model oil, for example decane. The water used may either be pure water or saline water, in order better to model the conditions in the mineral oil formation. The composition of the aqueous phase can be adjusted, for example, according to the composition of a particular deposit water.

Information regarding the aqueous phase used and the oil phase can be found below in the specific description of the tests.

Test Results

Surfactants based on linear $C_{16}C_{1-8}$-fatty alcohol were used. For comparison, surfactants based on the linear alcohols $C_{20}$ and $C_{14}$ were selected. A 1:1 mixture of decane and of an NaCl solution was admixed with butyl diethylene glycol (BDG). Butyl diethylene glycol (BDG) functions as a cosolvent and is not included in the calculation of SP*. To this was added a surfactant mixture composed of 3 parts alkyl alkoxysulfate and 1 part dodecylbenzene sulfonate (LUTENSIT® A-LBN 50 ex BASF). The total surfactant concentration is reported in percent by weight of the total volume.

In addition, interfacial tensions were measured directly by the spinning drop method on a dead crude oil (API approx. 14) and a saline original injection water with 11250 ppm TDS (total dissolved salt) at deposit temperature 32° C. For this purpose, the original injection water was admixed with 1000 ppm of surfactant, 500 ppm of BDG, 300 ppm of chelating agent and 3500 ppm of NaOH. At 32° C., an oil droplet was introduced into this clear solution and the interfacial tension was read off after 2 h. The results are shown in Tables 1 to 3.

TABLE 1

| Ex. | Alkyl-AO-SO$_4$Na:C$_{12}$H$_{25}$Ph-SO$_3$Na = 3:1 | Surfactant [%] | BDG [%] | NaCl [%] | $T_{opt}$ [° C.] | SP* | IFT [mN/m] |
|---|---|---|---|---|---|---|---|
| C1 | C$_{20}$—7PO—SO$_4$Na | 2.5 | 2 | 4 | 58 | 14.8 | 0.0014 |
| C2 | C$_{14}$—7PO—SO$_4$Na | 2.5 | 2 | 7 | 58 | 7.3 | 0.0056 |
| 3 | C$_{16}$C$_{18}$—7PO—SO$_4$Na | 2.5 | 2 | 4 | 60 | 17.8 | 0.0009 |
| 4 | C$_{16}$C$_{18}$—9PO—SO$_4$Na | 2.5 | 2 | 4 | 67 | 17.8 | 0.0009 |

As can be seen in Table 1, the $C_{16}C_{18}$ based compounds astonishingly gave the highest SP* values and hence the lowest interfacial tensions. In order to rule out any influence of temperature, comparison was first made at the same optimal temperature (formation of a balanced Winsor Type III microemulsion). As expected, Comparative Example C2 gives a higher interfacial tension than Example 3. This is in agreement with the literature. An extension of the linear alkyl radical beyond $C_{18}$ astonishingly already shows the differences thereof on the simple model oil decane (Comparative Example C1 compared to Examples 3 and 4). In the case of C1, the interfacial tension is not lowered any further, but increased. It can normally be inferred from the literature that an extension of the alkyl radical leads to a lower interfacial tension. However, this is not the case.

TABLE 2

| Ex. | Alkyl-AO-SO$_4$Na [1000 ppm] | BDG [ppm] | NaOH [ppm] | Chelate [ppm] | Salinity [ppm] | T [° C.] | Solubility |
|---|---|---|---|---|---|---|---|
| 1 | $C_{16}C_{18}$—7PO—SO$_4$Na | 500 | 3500 | 300 | 11250 | 32 | clear |
| 2 | $C_{16}C_{18}$—7PO—SO$_4$Na | 500 | 6500 | 300 | 11250 | 32 | clear |
| C3 | $C_{20}$—7PO—SO$_4$Na | 500 | 3500 | 300 | 11250 | 32 | turbid homogeneous |
| C4 | $C_{14}$—7PO—SO$_4$Na | 500 | 3500 | 300 | 11250 | 32 | clear |
| 5 | $C_{16}C_{18}$—6PO—SO$_4$Na | 500 | 3500 | 300 | 11250 | 32 | clear |
| C6 | $C_{20}$—6PO—SO$_4$Na | 500 | 3500 | 300 | 11250 | 32 | clear |
| C7 | $C_{20}$—9PO—SO$_4$Na | 500 | 5000 | 300 | 11250 | 32 | clear |

In the saline injection water, almost all surfactant formulations prepared have dissolved clearly at room temperature and deposit temperature 32° C. (Table 2). An exception is C3 containing $C_{20}$-7 PO-sulfate. A turbid but homogeneous solution was present here. This can lead over the course of time, in a porous matrix, to deposits and blockages of the fine channels. The lack of branching in the alkyl radical in the other examples is not found to be a disadvantage. The literature generally refers to the advantage of a branch. As a result, for example, the solubility improves, or the Kraft point of a surfactant is lowered. Surfactants based on linear alcohols do not have any disadvantages in terms of solubility as a result of the combination with propylene oxide.

TABLE 3

| Ex. | Alkyl-AO-SO$_4$Na [1000 ppm] | BDG [ppm] | NaOH [ppm] | Chelate [ppm] | Salinity [ppm] | T [° C.] | IFT [mN/m] |
|---|---|---|---|---|---|---|---|
| 1 | $C_{16}C_{18}$—7PO—SO$_4$Na | 500 | 3500 | 300 | 11250 | 32 | 0.0032 |
| 2 | $C_{16}C_{18}$—7PO—SO$_4$Na | 500 | 6500 | 300 | 11250 | 32 | 0.0028 |
| C3 | $C_{20}$—7PO—SO$_4$Na | 500 | 3500 | 300 | 11250 | 32 | 0.0604 |
| C4 | $C_{14}$—7PO—SO$_4$Na | 500 | 3500 | 300 | 11250 | 32 | 0.0373 |
| 5 | $C_{16}C_{18}$—6PO—SO$_4$Na | 500 | 3500 | 300 | 11250 | 32 | 0.0053 |
| C6 | $C_{20}$—6PO—SO$_4$Na | 500 | 3500 | 300 | 11250 | 32 | 0.0340 |
| C7 | $C_{20}$—9PO—SO$_4$Na | 500 | 5000 | 300 | 11250 | 32 | 0.0611 |

As can be seen in Table 3, the surfactants based on linear alcohols give different interfacial tensions with respect to the crude oil. Even in the case of variation in the amount of NaOH (and hence a change in the salinity and an altered mobilization of naphthenic acids as natural surfactants), Example 1 and Example 2 give excellent interfacial tensions of about $3 \times 10^{-3}$ mN/m. Even a variation in the degree of propoxylation (Example 5) shows only a small change in the good interfacial tension values. It rises to $5 \times 10^{-3}$ mN/m. If this is compared with a surfactant based on the linear $C_{20}$-alcohol (C6 and C7), it is found that the interfacial tensions are much higher (at $3-6 \times 10^{-2}$ mN/n, almost one order of magnitude higher). A surfactant with a shorter alkyl moiety ($C_{14}$), as can seen from C4, also does not give better interfacial tension values.

The invention claimed is:

1. A process for mineral oil production by means of Winsor type III microemulsion flooding, in which an aqueous surfactant formulation comprising at least one ionic surfactant, for the purpose of lowering the interfacial tension between oil and water to <0.1 mN/m, is injected through at least one injection borehole into a mineral oil deposit, and crude oil is withdrawn from the deposit through at least one production borehole, wherein the surfactant formulation comprises at least one surfactant of the general formula $$R^1\text{—O—}(CH_2C(CH_3)HO)_m(CH_2CH_2O)_n\text{—}XY^-M^+$$

where $R^1$ is an unbranched saturated or unsaturated straight-chain aliphatic hydrocarbon radical having 16 to 18 carbon atoms, n is from 0 to 99, m is from 0 to 99, where the sum of n and m is in the range from 3 to 99, $Y^-$ is selected from the group of sulfate groups, sulfonate groups, carboxylate groups and phosphate groups, X is an alkyl or alkylene group having 0 to 10 carbon atoms, and $M^+$ is a cation.

2. The process according to claim 1, wherein $R^1$ is an unbranched saturated straight-chain aliphatic hydrocarbon radical having 16 to 18 carbon atoms, $Y^-$ is selected from the group of sulfate groups, sulfonate groups and carboxylate groups, in the presence of both alkylene oxides in the surfactant the alkylene oxides are >80% arranged in block form, the propylene oxide block is joined directly to the above-described $R^1$—O, and the sum of n and m is in the range from 5 to 15.

3. The process according to claim 1, wherein m is greater than n.

4. The process according to claim 1, wherein the concentration of all surfactants together is 0.05 to 5% by weight, based on the total amount of the aqueous surfactant formulation.

* * * * *